United States Patent [19]

Wu et al.

[11] Patent Number: 6,110,859
[45] Date of Patent: Aug. 29, 2000

[54] HYBRID CATALYST SYSTEM FOR CONVERTING HYDROCARBONS AND A METHOD OF MAKING AND USING SUCH CATALYST SYSTEM

[75] Inventors: An-hsiang Wu, Bartlesville; Charles A. Drake, Nowata, both of Okla.

[73] Assignee: Phillips Petroleum Company, Bartlesville, Okla.

[21] Appl. No.: 09/192,742

[22] Filed: Nov. 16, 1998

[51] Int. Cl.[7] ............ C01G 23/00; C01G 25/00; C01G 27/00; C01G 33/00; C01G 35/00
[52] U.S. Cl. ............ 502/103; 502/152; 502/177; 585/734; 585/747; 585/748; 585/749; 585/750
[58] Field of Search ................ 502/103, 152, 502/177; 585/734, 747, 748, 749, 750

[56] References Cited

U.S. PATENT DOCUMENTS

| | | | |
|---|---|---|---|
| 4,219,445 | 8/1980 | Finch | 252/443 |
| 4,325,843 | 4/1982 | Slaugh et al. | 252/443 |
| 5,330,944 | 7/1994 | Sherif et al. | 502/64 |
| 5,776,852 | 7/1998 | Wu et al. | 502/177 |

*Primary Examiner*—Mark L. Bell
*Assistant Examiner*—Michael J. Di Verdi
*Attorney, Agent, or Firm*—Jeffrey R. Anderson

[57] ABSTRACT

A catalyst system comprising a first solid material comprising activated carbon and at least one carburized transition metal; and a second solid material comprising at least one halogen component and alumina, and a method of preparing such catalyst system which comprises mixing a first solid material comprising activated carbon and at least one carburized transition metal and a second solid material comprising at least one halogen component and alumina are disclosed. The thus-obtained catalyst system is employed as a catalyst in the isomerization of a hydrocarbon feedstock comprising saturated hydrocarbons.

57 Claims, No Drawings

HYBRID CATALYST SYSTEM FOR CONVERTING HYDROCARBONS AND A METHOD OF MAKING AND USING SUCH CATALYST SYSTEM

This invention relates to catalyst systems useful in hydrocarbon upgrading processes and to methods for their production and use. In another aspect, this invention relates to processes for isomerizing hydrocarbons employing the novel catalyst systems of this invention.

Catalysts and process technology for the isomerization of saturated hydrocarbons are known in the art, and are described in the patent literature, e.g. in U.S. Pat. Nos. 5,004,859, 5,536,692 and 5,591,689.

Such catalysts typically contain platinum. One concern with using platinum-containing catalysts in the isomerization of saturated hydrocarbons is the sensitivity of platinum to poisons such as oxygen, nitrogen and sulfur. Therefore, it is desirable to develop catalyst systems which are less sensitive to such poisons than platinum-containing catalysts when used in the isomerization of saturated hydrocarbons.

It is also desirable to develop economical and efficient methods of making improved isomerization catalysts.

SUMMARY OF THE INVENTION

It is an object of this invention to provide a novel hybrid catalyst system effective for at least partially isomerizing saturated hydrocarbons which is less sensitive to catalyst poisons such as oxygen, nitrogen and sulfur than platinum-containing catalysts.

It is another object of this invention to provide an improved method of preparing a catalyst system, effective for at least partially isomerizing saturated hydrocarbons, which is economical and efficient.

It is a further object of this invention to employ this novel hybrid catalyst system as a catalyst in the at least partial isomerization of saturated hydrocarbons.

It is still another object of the present invention to provide an improved isomerization process of increased efficiency.

According to a first embodiment of the present invention, a catalyst system which can be used for at least partially isomerizing a hydrocarbon feedstock comprising saturated hydrocarbons is provided. The novel catalyst system comprises a first solid material comprising activated carbon and at least one carburized transition metal, and a second solid material comprising at least one halogen component and alumina. The term "transition metal", as used herein, includes, but is not limited to, titanium, zirconium, hafnium, vanadium, niobium, tantalum, chromium, molybdenum and tungsten.

According to a second embodiment of the present invention, a method which can be used for producing a catalyst system is provided. The method comprises blending a first solid material comprising activated carbon and at least one carburized transition metal and a second solid material comprising at least one halogen component and alumina.

According to a third embodiment of the present invention, a process is provided for the at least partial isomerization of a hydrocarbon feedstock comprising saturated hydrocarbons by contacting under conversion conditions the hydrocarbon feedstock with a novel catalyst system prepared by the method of the second embodiment.

Other objects and advantages will become apparent from the detailed description and the appended claims.

DETAILED DESCRIPTION OF THE INVENTION

According to the first embodiment of the present invention, the catalyst system can comprise, consist essentially of, or consist of a first solid material comprising activated carbon and at least one carburized transition metal and a second solid material comprising, or consisting essentially of, or consisting of at least one halogen component and alumina.

Considering first the first solid material, any suitable activated carbon material can be used in preparing the first solid material. The activated carbon generally has a surface area in the range of from about 800 to about 1800 $m^2/g$ and a particle size in the range of from about 4 to about 40 mesh, according to Perry's Chemical Engineers Handbook, Sixth Edition, p. 16–9.

An essential ingredient of the first solid material is at least one carburized transition metal including, but not limited to, carburized titanium, carburized zirconium, carburized hafnium, carburized vanadium, carburized niobium, carburized tantalum, carburized chromium, carburized molybdenum, carburized tungsten and combinations of any two or more thereof. This at least one carburized transition metal can be present in the first solid material in any amount that is catalytically effective. Generally, the amount of elemental transition metal (which is contained in the at least one carburized transition metal) present in the first solid material is in the range of upwardly to about 50 weight %, preferably in the range of from about 1 weight % to about 40 weight %, and most preferably from 5 weight % to 30 weight % based on the total weight of the first solid material, measured on an elemental transition metal basis. Preferably, the at least one carburized transition metal is of the formula $X_2C$, wherein X is the transition metal and C is carbon.

The preferred carburized transition metal for the first solid material is carburized tungsten, even more preferably, ditungsten carbide of the formula $W_2C$, wherein W is tungsten and C is carbon.

Considering next the second solid material, any suitable alumina material can be used in preparing the second solid material. Suitable aluminas include (but are not limited to) hydrated aluminas (such as boehmite, pseudoboehmite, bayerite), alpha-alumina, beta-alumina, gamma-alumina, delta-alumina, eta-alumina and theta-alumina, preferably gamma-alumina. The alumina material generally has a surface area (determined by the BET method of Brunauer, Emmett and Teller employing $N_2$) in the range of from about 100 to about 400 $m^2/g$, a pore volume (measured by nitrogen intrusion porosimetry) in the range of from about 0.2 to about 1.0 $cm^3/g$, and a particle size in the range of from about 8 to about 200 mesh.

An essential ingredient of the second solid material is at least one halogen component. The at least one halogen component can be present in the second solid material in any amount that is catalytically effective. Generally, the amount of halogen present in the second solid material is in the range of from about 0.1 to about 50 weight %; preferably in the range of from about 0.5 to about 30 weight %; and most preferably from 1 to 10 weight % based on the total weight of the second solid material, measured on an elemental halogen basis.

Examples of suitable halogen components include, but are not limited to, inorganic aluminum chloride compounds such as aluminum chloride, and organic aluminum chloride compounds such as ethyl aluminum dichloride, methylaluminum dichloride, methylaluminum sesquichloride, dimethylaluminum chloride, ethylaluminum sesquichloride, diethylaluminum chloride, and mixtures of any two or more thereof. Presently preferred are ethylaluminum dichloride and aluminum chloride.

All weight percents of components of the catalyst system can be measured using X-Ray fluorescence analysis, as described in "Spectrometry: Principles and Practices in X-Ray Spectrometric Analysis" by Eugene Burton, 2nd edition.

According to the second embodiment of the present invention, the catalyst system can be prepared by the following method.

Considering first the preparation of the first solid material, at least one transition metal compound can be incorporated into the activated carbon by any suitable means or method known in the art for incorporating metallic elements into a substrate material to thereby form a transition metal-activated carbon compound.

Examples of suitable transition metal compounds include, but are not limited to, ammonium polytungstate, ammonium paratungstate, ammonium tetrathiotungstate (VI), bis (cyclopentadienyl)tungsten dichloride, bis(i-propylcyclopentadienyl)tungsten dihydride, cyclopentadienyltungsten tricarbonyl dimer, mesitylene tungsten tricarbonyl, tungsten (IV) chloride, tungsten (VI) chloride, tungstic acid, 12-tungstophosphoric acid hydrate, titanium (IV) bromide, titanium (IV) n-butoxide, titanium (IV) t-butoxide, titanium (IV) chloride, titanium (di-i-propoxide) bis(acetylacetonate), titanium (IV) ethoxide, titanium (IV) 2-ethylhexoxide, titanium (IV) i-propoxide, tris (2,2,6,6-tetramethyl-3,5-heptanedionato)titanium (III), zirconium (IV) bromide, zirconium (IV) n-butoxide, zirconium (IV) t-butoxide, zirconium (IV) chloride, zirconium (IV) dichloride oxide hydrate, zirconium (IV) dinitrate oxide hydrate, zirconium (IV) ethoxide, hafnium (IV) chloride, hafnium (IV) dichloride oxide octahydrate, hafnium (IV) ethoxide, hafnium (IV) i-propoxide monoisopropylate, vanadium (III) chloride, vanadium (V) trichloride oxide, vanadium (V) tri-i-propoxy oxide, niobium (V) bromide, niobium (V) chloride, niobium (V) ethoxide, tantalum (V) chloride, tantalum (V) ethoxide, tantalum (V) methoxide, chromium (III) acetate, chromium (III) acetylacetonate, chromium (III) bromide hexahydrate, chromium (III) chloride, chromium (III) 2-ethylhexanoate, chromium (III) naphthenate, chromium (III) nitrate nonahydrate, chromium (III) sulfate hydrate, ammonium molybdate tetrahydrate, molybdenum (II) acetate dimer, molybdenum carbonyl, molybdenum (V) chloride, molybdenum (VI) dioxide bis(acetylacetonate), 12-molybdophosphoric acid hydrate and combinations of any two or more thereof.

It is preferred to use any standard incipient wetness technique for impregnating the activated carbon with the at least one transition metal compound. A preferred method uses a liquid impregnation solution containing the desirable concentration of at least one transition metal compound. It is particularly desirable to use an aqueous solution formed by dissolving at least one transition metal compound in water. It is preferable to use somewhat of an acidic solution to aid in the dissolution of the at least one transition metal compound. The acid used to acidify the impregnation solution is preferably citric acid.

Generally, the transition metal-activated carbon compound is dried in the presence of air at a temperature in the range of from about 20° C. to about 200° C. for a time period in the range of from about 0.1 hour to about 30 hours.

The transition metal-activated carbon compound, which may or may not have been dried, can be carburized under conditions suitable for converting at least a portion of the at least one transition metal compound to at least one carburized transition metal, preferably, of the formula $X_2C$, wherein X is the transition metal and C is carbon, thereby forming the first solid material comprising a carburized transition metal-activated carbon compound. The carburization conditions more particularly include a temperature in the range of from about 300° C. to about 1,500° C., preferably from about 400° C. to about 1,200° C., and most preferably from 500° C. to 1000° C. The carburization is preferably performed in the presence of a gas comprising methane and hydrogen for a time period in the range of from about 0.1 hour to about 30 hours, preferably from about 2 hours to about 20 hours, and most preferably from 3 hours to 15 hours.

It is believed that carburization of the at least one transition metal compound enhances the catalytic activity of the catalyst system and decreases the catalyst systems' sensitivity to poisons such as oxygen, nitrogen and sulfur.

Considering now the preparation of the second solid material, the alumina can be calcined under conditions suitable to thereby provide a calcined alumina. The calcination conditions include a temperature in the range of from about 250° C. to about 1,000° C., preferably from about 350° C. to about 750° C., and most preferably from 450° C. to 650° C. and a pressure in the range of from about 0.5 to about 50 atmospheres (atm), preferably from about 0.5 to about 30 atm, and most preferably from 0.5 to 10 atm. The calcination can be performed in either an air atmosphere, or an inert atmosphere, or a combination thereof for a time period in the range of from about 0.1 hour to about 30 hours, preferably from about 2 hours to about 20 hours, and most preferably from 3 hours to 15 hours.

The calcined alumina is then contacted, in any suitable manner, with the at least one halogen component, as described above, to thereby form the second solid material. These halogen components are easily hydrolyzed and thus should be handled and applied in a dry environment. Preferably, they are dissolved in a dry organic hydrocarbon solvent, such as in a $C_6$ to $C_{10}$ cycloalkane, benzene, toluene, ethylbenzene, xylene(s) and the like. The presently preferred solvent is cyclohexane. The solution containing the at least one halogen component and the hydrocarbon solvent is then contacted with the calcined alumina to incorporate the at least one halogen component into the calcined alumina.

Another method of contacting the calcined alumina with such at least one halogen component includes placing the calcined alumina in a contactor directly above a quantity of the at least one halogen component, preferably in solid form, and passing a helium gas stream up through the at least one halogen component first and then through the calcined alumina compound under conditions suitable to sublime the at least one halogen component into the helium gas stream and to then deposit the at least one halogen component into the interstitial spaces of the calcined alumina. The conditions more particularly include heating the contactor contents to a temperature in the range of from about 300° C. to about 1000° C., preferably from about 400° C. to about 900° C., and most preferably from 500° C. to 800° C., and passing a helium gas stream up through the at least one halogen component first and then through the calcined alumina compound for a time period in the range of from about 1 hour to about 30 hours, preferably from about 2 hours to about 20 hours, and most preferably from 3 hours to 15 hours.

The catalyst system of the present invention can be produced by combining the first solid material and the second solid material by any means known to those skilled in the art such as, but not limited, stirring or blending, preferably in a dry, inert gas atmosphere. The weight ratio of the first solid material to the second solid material in the finished catalyst system is in the range of from about 1:40 to about 10:1, preferably from about 1:20 to about 4:1, and most preferably from 1:10 to 3:1.

According to the third embodiment of the present invention, the inventive catalyst system is generally employed in the isomerization of a hydrocarbon feedstock comprising saturated hydrocarbons (preferably normal alkanes). Examples of suitable hydrocarbon feedstocks include, but are not limited to, normal butane, normal pentane, normal hexane, normal heptane, normal octane, cyclohexane, methylcyclopentane, cycloheptane, methylcycloheptane and the like, and combinations of any two or more thereof.

Generally, hydrogen is mixed with the hydrocarbon feedstock to form a feed mixture which is contacted with the catalyst system, prepared by the method disclosed in the second embodiment of this invention, contained in an isomerization zone. The concentration of the hydrogen in the feed mixture during this contacting step shall be such as to provide a hydrogen to saturated hydrocarbon molar ratio of at least about 0.01:1, preferably about 0.01:1 to about 5:1, and most preferably from 0.02:1 to 2:1. The hydrocarbon feedstock and hydrogen can be contacted with the inventive catalyst system by any suitable manner. The contacting step can be operated as a batch process step or, preferably, as a continuous process step. In the latter operation, a solid catalyst bed or a moving catalyst bed or a fluidized catalyst bed can be employed. Any of these operational modes have advantages and disadvantages, and those skilled in the art can select the one most suitable for a particular feed and catalyst.

The contacting step is preferably carried out within the isomerization zone, wherein is contained the inventive catalyst system, and under reaction conditions that suitably promote isomerization of at least a portion of the saturated hydrocarbons of the hydrocarbon feedstock. The reaction temperature of the isomerization zone is more particularly in the range of from about 50° C. to about 260° C., preferably from about 90° C. to about 200° C., and most preferably from 100° C. to 150° C. The contacting pressure of the isomerization zone is within the range of from about 200 psig to about 1500 psig, preferably from about 250 psig to about 1000 psig, and most preferably from 300 psig to 750 psig.

The flow rate at which the hydrocarbon feedstock is charged to the isomerization zone is such as to provide a weight hourly space velocity ("WHSV") in the range of from exceeding 0 hour$^{-1}$ upwardly to about 1000 hour$^{-1}$. The term "weight hourly space velocity", as used herein, shall mean the numerical ratio of the rate at which a hydrocarbon feedstock is charged to the isomerization zone in pounds per hour divided by the pounds of catalyst contained in the isomerization zone to which the hydrocarbon feedstock is charged. The preferred WHSV of the hydrocarbon feedstock to the isomerization zone is preferably in the range of from about 0.25 hour$^{-1}$ to about 250 hour$^{-1}$ and, most preferably, from 0.5 hour$^{-1}$ to 100 hour$^{-1}$.

In order to activate the catalyst system and to retard its deactivation during the isomerization reaction, chloride is frequently added to the feed mixture in an amount such that the chloride is present in the feed mixture in the range of from about 0.001 weight % to about 1 weight % based on the total weight of the feed mixture. The chloride is generally in the form of hydrogen chloride or at least one chloroalkane, preferably carbon tetrachloride, chloroform, ethylchloride or isopropylchloride.

The following examples are presented to further illustrate the invention and are not to be construed as unduly limiting its scope.

EXAMPLE I

This example illustrates the preparation of catalysts which were subsequently tested as catalysts in the isomerization of n-butane to iso-butane.

Catalyst A (control)

An 11.1 gram quantity of a commercially available activated carbon (in the form of 1/16" extrudates provided by Sigma-Aldrich Co., under product designation Darco®) was impregnated, by incipient wetness, with an aqueous solution containing 2.4 grams of ammonium polytungstate (($NH_4$)$_4$ $H_2W_{12}O_{40}$) and 9.5 grams of water. The thus obtained impregnated activated carbon was dried at a temperature of about 125° C. for about 16 hours. The thus obtained dried, impregnated activated carbon was carburized by passing methane and hydrogen gas streams over the dried, impregnated activated carbon at flow rates of 150 ml/min and 600 ml/min; respectively, at a temperature of 750° C. for 6 hours.

Catalyst B (control)

A 50 gram quantity of a commercially available alumina, in the form of 1/16" extrudates (provided by United Catalysts, Inc., Louisville, Ky., under product designation "UCI-331-4"), was calcined at a temperature of about 538° C. for 6 hours followed by heating at a temperature of about 120° C. for 64 hours. The thus obtained calcined alumina was placed in a quartz calcine tube as a fixed bed directly above a quantity of aluminum chloride. The calcined alumina and aluminum chloride were heated to a temperature of about 650° C. and a 300 ml/min helium gas stream was passed upwardly through the aluminum chloride and the calcined alumina for a time period of 6 hours.

EXAMPLE II

This example illustrates the use of the catalysts described in Example I in the isomerization of n-butane.

In Run 1, a 2.5 gram sample of Catalyst A described in Example I was placed into a stainless steel tube reactor (length: about 18 inches; inner diameter: about 0.5 inch). The steel reactor tube was heated to about 110° C. A stream of hydrogen gas was passed through the catalyst bed at a rate of 12.0 liters/hour. The reactor pressure was about 500 psig. Liquid n-butane was introduced at a rate of 6.0 liters/hour while the flow of hydrogen gas was maintained at 12.0 liters/hour so as to provide a mole ratio of $H_2$ to n-butane of about 2.2:1. Carbon tetrachloride was injected into the feed mixture at a rate of 0.89 microliters/hour. The isomerization product was analyzed by means of a gas chromatograph. Test data results obtained after 7 hours on stream are summarized in the Table.

In Run 2, a 2.6 gram sample of Catalyst B described in Example I was placed into a stainless steel tube reactor (length: about 18 inches; inner diameter: about 0.5 inch). The steel reactor tube was heated to about 110° C. A stream of hydrogen gas was passed through the catalyst bed at a rate of 12.0 liters/hour. The reactor pressure was about 500 psig. Liquid n-butane was introduced at a rate of 6.0 liters/hour while the flow of hydrogen gas was maintained at 12.0 liters/hour so as to provide a mole ratio of $H_2$ to n-butane of about 2.2:1. Carbon tetrachloride was injected into the feed mixture at a rate of 0.89 microliters/hour. The isomerization product was analyzed by means of a gas chromatograph. Test data results obtained after 7 hours on stream are summarized in the Table.

In Run 3, a 1.1 gram sample of Catalyst A was premixed (physical mixing) with a 2.6 gram sample of Catalyst B, both described in Example I. The mixture was placed into a stainless steel tube reactor (length: about 18 inches; inner diameter: about 0.5 inch). The steel reactor tube was heated to about 110° C. A stream of hydrogen gas was passed through the catalyst bed at a rate of 12.0 liters/hour. The reactor pressure was about 500 psig. Liquid n-butane was introduced at a rate of 6.0 liters/hour while the flow of hydrogen gas was maintained at 12.0 liters/hour so as to provide a mole ratio of $H_2$ to n-butane of about 2.2:1. Carbon tetrachloride was injected into the feed mixture at a rate of 0.89 microliters/hour. The isomerization product was analyzed by means of a gas chromatograph. Test data results obtained after 7 hours on stream are summarized in the Table.

TABLE

| Run | Catalyst | % of Isobutane in Product | % of Isobutane in Product less n-butane |
|---|---|---|---|
| 1 | A (control) | 0 | 0 |
| 2 | B (control) | 0 | 0 |
| 3 | A + B (invention) (physically mixed) | 10.8 | 99.2 |

The test data presented in the Table show that the use of the inventive catalyst in Run 3 resulted in considerably increased n-butane isomerization than control Catalysts A (Run 1) and B (Run 2) used alone.

Control Runs 1 and 2 demonstrated that Catalysts A and B used alone were ineffective in n-butane isomerization.

Additionally, the percent iso-butane in product for the inventive catalyst used in Run 3 is comparable to the percent iso-butane in product for typical platinum containing isomerization catalysts, which range from about 6% to about 18% iso-butane in product, as presented in examples in U.S. Pat. Nos. 5,536,692 at column 6 and 5,591,689 at column 8. Thus, use of the inventive catalyst system, comprising a first solid material comprising activated carbon and at least one carburized transition metal and a second solid material comprising at least one halogen component and alumina, results in n-butane conversions to iso-butane comparable to that for platinum containing isomerization catalysts but with a decreased sensitivity to poisons such as oxygen, nitrogen and sulfur as compared to the platinum containing isomerization catalysts.

Reasonable variations, modifications, and adaptations can be made within the scope of the disclosure and the appended claims without departing from the scope of this invention.

That which is claimed is:

1. A catalyst system comprising:
   a first solid material comprising activated carbon and at least one carburized transition metal; and
   a second solid material comprising at least one halogen component and alumina.

2. A catalyst system as recited in claim 1 wherein said at least one carburized transition metal is of the formula $X_2C$, wherein X is a transition metal and C is carbon.

3. A catalyst system as recited in claim 1 wherein said alumina is calcined alumina.

4. A catalyst system as recited in claim 1 wherein said at least one halogen component comprises chlorine.

5. A catalyst system as recited in claim 1 wherein said first solid material comprises a transition metal selected from the group consisting of titanium, zirconium, hafnium, vanadium, niobium, tantalum, chromium, molybdenum, tungsten and combinations of any two or more thereof in an amount in the range of from about 0.1 weight % to about 50 weight % based on the total weight of said first solid material.

6. A catalyst system as recited in claim 1 wherein said second solid material contains halogen in an amount in the range of from about 0.1 weight % to about 50 weight % based on the total weight of said second solid material.

7. A catalyst system as recited in claim 1 wherein said carburized transition metal comprises carburized titanium.

8. A catalyst system as recited in claim 1 wherein said carburized transition metal comprises carburized zirconium.

9. A catalyst system as recited in claim 1 wherein said carburized transition metal comprises carburized hafnium.

10. A catalyst system as recited in claim 1 wherein said carburized transition metal comprises carburized vanadium.

11. A catalyst system as recited in claim 1 wherein said carburized transition metal comprises carburized niobium.

12. A catalyst system as recited in claim 1 wherein said carburized transition metal comprises carburized tantalum.

13. A catalyst system as recited in claim 1 wherein said carburized transition metal comprises carburized chromium.

14. A catalyst system as recited in claim 1 wherein said carburized transition metal comprises carburized molybdenum.

15. A catalyst system as recited in claim 1 wherein said carburized transition metal comprises carburized tungsten.

16. A catalyst system as recited in claim 1 wherein the weight ratio of said first solid material to said second solid material is in the range of from about 1:40 to about 10:1.

17. A catalyst system prepared by the method of blending a first solid material comprising activated carbon and at least one carburized transition metal and a second solid material comprising at least one halogen component and alumina.

18. A catalyst system as recited in claim 17 wherein said first solid material is prepared by the steps of:
   mixing said activated carbon and at least one transition metal compound to form a mixture; and
   carburizing said mixture to form said first solid material.

19. A catalyst system as recited in claim 18 wherein said at least one transition metal compound comprises a compound selected from the group consisting of ammonium polytungstate, ammonium paratungstate, ammonium tetrathiotungstate (VI), bis(cyclopentadienyl)tungsten dichloride, bis(i-propylcyclopentadienyl)tungsten dihydride, cyclopentadienyltungsten tricarbonyl dimer, mesitylene tungsten tricarbonyl, tungsten (IV) chloride, tungsten (VI) chloride, tungstic acid, 12-tungstophosphoric acid hydrate, titanium (IV) bromide, titanium (IV) n-butoxide, titanium (IV) t-butoxide, titanium (IV) chloride, titanium (di-i-propoxide)bis(acetylacetonate), titanium (IV) ethoxide, titanium (IV) 2-ethylhexoxide, titanium (IV) i-propoxide, tris (2,2,6,6-tetramethyl-3,5-heptanedionato) titanium (III), zirconium (IV) bromide, zirconium (IV) n-butoxide, zirconium (IV) t-butoxide, zirconium (IV) chloride, zirconium (IV) dichloride oxide hydrate, zirconium (IV) dinitrate oxide hydrate, zirconium (IV) ethoxide, hafnium (IV) chloride, hafnium (IV) dichloride oxide octahydrate, hafnium (IV) ethoxide, hafnium (IV) i-propoxide monoisopropylate, vanadium (III) chloride, vanadium (V) trichloride oxide, vanadium (V) tri-i-propoxy oxide, niobium (V) bromide, niobium (V) chloride, niobium (V) ethoxide, tantalum (V) chloride, tantalum (V) ethoxide, tantalum (V) methoxide, chromium (III) acetate, chromium (III) acetylacetonate, chromium (III) bromide hexahydrate, chromium (III) chloride, chromium (III) 2-ethylhexanoate, chromium (III) naphthenate, chromium (III) nitrate nonahydrate, chromium (III) sulfate hydrate, ammonium molybdate tetrahydrate, molybdenum (II) acetate dimer, molybdenum carbonyl, molybdenum (V) chloride, molybdenum (VI) dioxide bis(acetylacetonate), 12-molybdophosphoric acid hydrate and combinations of any two or more thereof.

20. A catalyst system as recited in claim 18 wherein said carburizing step comprises heating said mixture at a temperature in the range of from about 300° C. to about 1200° C. in the presence of methane and hydrogen.

21. A catalyst system as recited in claim 17 wherein said at least one halogen component comprises chlorine.

22. A catalyst system as recited in claim 17 wherein said second solid material is prepared by the steps of:
calcining said alumina to form a calcined alumina; and
incorporating said at least one halogen component into said calcined alumina to form said second solid material.

23. A catalyst system as recited in claim 22 wherein said step of incorporating said at least one halogen component comprises contacting said calcined alumina with a compound selected from the group consisting of aluminum chloride, ethyl aluminum dichloride, methylaluminum dichloride, methylaluminum sesquichloride, dimethylaluminum chloride, ethylaluminum sesquichloride, diethylaluminum chloride, and combinations of any two or more thereof to form said second solid material.

24. A catalyst system as recited in claim 17 wherein said first solid material comprises a transition metal selected from the group consisting of titanium, zirconium, hafnium, vanadium, niobium, tantalum, chromium, molybdenum, tungsten and combinations of any two or more thereof in an amount in the range of from about 0.1 weight % to about 50 weight % based on the total weight of said first solid material.

25. A catalyst system as recited in claim 17 wherein said second solid material contains halogen in an amount in the range of from about 0.1 weight % to about 50 weight % based on the total weight of said second solid material.

26. A catalyst system as recited in claim 17 wherein said carburized transition metal comprises carburized titanium.

27. A catalyst system as recited in claim 17 wherein said carburized transition metal comprises carburized zirconium.

28. A catalyst system as recited in claim 17 wherein said carburized transition metal comprises carburized hafnium.

29. A catalyst system as recited in claim 17 wherein said carburized transition metal comprises carburized vanadium.

30. A catalyst system as recited in claim 17 wherein said carburized transition metal comprises carburized niobium.

31. A catalyst system as recited in claim 17 wherein said carburized transition metal comprises carburized tantalum.

32. A catalyst system as recited in claim 17 wherein said carburized transition metal comprises carburized chromium.

33. A catalyst system as recited in claim 17 wherein said carburized transition metal comprises carburized molybdenum.

34. A catalyst system as recited in claim 17 wherein said carburized transition metal comprises carburized tungsten.

35. A catalyst system as recited in claim 17 wherein the weight ratio of said first solid material to said second solid material is in the range of from about 1:40 to about 10:1.

36. A method of preparing a catalyst system which comprises blending a first solid material comprising activated carbon and at least one carburized transition metal and a second solid material comprising at least one halogen component and alumina.

37. A method as recited in claim 36 wherein said first solid material is prepared by the steps of:
mixing said activated carbon with at least one transition metal compound to form a transition metal-activated carbon compound; and
carburizing said transition metal-activated carbon compound to form said first solid material.

38. A method as recited in claim 37 wherein said at least one transition metal compound comprises a compound selected from the group consisting of ammonium polytungstate, ammonium paratungstate, ammonium tetrathiotungstate (VI), bis(cyclopentadienyl)tungsten dichloride, bis(i-propylcyclopentadienyl)tungsten dihydride, cyclopentadienyltungsten tricarbonyl dimer, mesitylene tungsten tricarbonyl, tungsten (IV) chloride, tungsten (VI) chloride, tungstic acid, 12-tungstophosphoric acid hydrate, titanium (IV) bromide, titanium (IV) n-butoxide, titanium (IV) t-butoxide, titanium (IV) chloride, titanium (di-i-propoxide)bis(acetylacetonate), titanium (IV) ethoxide, titanium (IV) 2-ethylhexoxide, titanium (IV) i-propoxide, tris (2,2,6,6-tetramethyl-3,5-heptanedionato) titanium (III), zirconium (IV) bromide, zirconium (IV) n-butoxide, zirconium (IV) t-butoxide, zirconium (IV) chloride, zirconium (IV) dichloride oxide hydrate, zirconium (IV) dinitrate oxide hydrate, zirconium (IV) ethoxide, hafnium (IV) chloride, hafnium (IV) dichloride oxide octahydrate, hafnium (IV) ethoxide, hafnium (IV) i-propoxide monoisopropylate, vanadium (III) chloride, vanadium (V) trichloride oxide, vanadium (V) tri-i-propoxy oxide, niobium (V) bromide, niobium (V) chloride, niobium (V) ethoxide, tantalum (V) chloride, tantalum (V) ethoxide, tantalum (V) methoxide, chromium (III) acetate, chromium (III) acetylacetonate, chromium (III) bromide hexahydrate, chromium (III) chloride, chromium (III) 2-ethylhexanoate, chromium (III) naphthenate, chromium (III) nitrate nonahydrate, chromium (III) sulfate hydrate, ammonium molybdate tetrahydrate, molybdenum (II) acetate dimer, molybdenum carbonyl, molybdenum (V) chloride, molybdenum (VI) dioxide bis(acetylacetonate), 12-molybdophosphoric acid hydrate and combinations of any two or more thereof.

39. A method as recited in claim 37 wherein said carburizing step comprises heating said mixture at a temperature in the range of from about 300° C. to about 1200° C. in the presence of methane and hydrogen.

40. A method as recited in claim 36 wherein said at least one halogen component comprises chlorine.

41. A method as recited in claim 36 wherein said second solid material is prepared by the steps of:
calcining said alumina to form a calcined alumina; and
incorporating said at least one halogen component into said calcined alumina to form said second solid material.

42. A method as recited in claim 41 wherein said step of incorporating said at least one halogen component comprises contacting said calcined alumina with a compound selected from the group consisting of aluminum chloride, ethyl aluminum dichloride, methylaluminum dichloride, methylaluminum sesquichloride, dimethylaluminum chloride, ethylaluminum sesquichloride, diethylaluminum chloride, and combinations of any two or more thereof to form said second solid material.

43. A method as recited in claim 36 wherein said first solid material comprises a transition metal selected from the group consisting of titanium, zirconium, hafnium, vanadium, niobium, tantalum, chromium, molybdenum, tungsten and combinations of any two or more thereof in an amount in the range of from about 0.1 weight % to about 50 weight % based on the total weight of said first solid material.

44. A method as recited in claim 36 wherein said second solid material contains halogen in an amount in the range of from about 0.1 weight % to about 50 weight % based on the total weight of said second solid material.

45. A method as recited in claim 36 wherein said carburized transition metal comprises carburized titanium.

46. A method as recited in claim 36 wherein said carburized transition metal comprises carburized zirconium.

47. A method as recited in claim 36 wherein said carburized transition metal comprises carburized hafnium.

48. A method as recited in claim 36 wherein said carburized transition metal comprises carburized vanadium.

49. A method as recited in claim 36 wherein said carburized transition metal comprises carburized niobium.

50. A method as recited in claim 36 wherein said carburized transition metal comprises carburized tantalum.

51. A method as recited in claim 36 wherein said carburized transition metal comprises carburized chromium.

52. A method as recited in claim 36 wherein said carburized transition metal comprises carburized molybdenum.

53. A method as recited in claim 36 wherein said carburized transition metal comprises carburized tungsten.

54. A method as recited in claim 36 wherein the weight ratio of said first solid material to said second solid material is in the range of from about 1:40 to about 10:1.

55. A process for isomerizing at least a portion of a hydrocarbon feedstock comprising saturated hydrocarbons which comprises contacting said hydrocarbon feedstock at a temperature in the range of from about 50° C. to about 260° C. with a composition comprising:

a first solid material comprising activated carbon and at least one carburized transition metal; and a second solid material comprising at least one halogen component and alumina.

56. A process as recited in claim 55 wherein said composition is the catalyst system of claims 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35.

57. A process as recited in claim 55 wherein said composition is prepared by the method of claims 36, 37, 38, 39, 40, 41, 42, 43, 44, 45, 46, 47, 48, 49, 50, 51, 52, 53 or 54.

* * * * *